United States Patent
Deshpande et al.

(10) Patent No.: US 9,984,543 B2
(45) Date of Patent: May 29, 2018

(54) ANOMALY DETECTION SYSTEM AND METHOD

(71) Applicant: Tata Consultancy Services Limited, Mumbai (IN)

(72) Inventors: Parijat Deshpande, Pune (IN); Ramu Vempada, Karnataka (IN); Ranjan Dasgupta, Kolkata (IN); Arpan Pal, Kolkata (IN); Dibyendu Roy, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 0 days. days.

(21) Appl. No.: 15/552,225

(22) PCT Filed: Feb. 16, 2016

(86) PCT No.: PCT/IB2016/050810
§ 371 (c)(1),
(2) Date: Aug. 18, 2017

(87) PCT Pub. No.: WO2016/132282
PCT Pub. Date: Aug. 25, 2016

(65) Prior Publication Data
US 2018/0038954 A1 Feb. 8, 2018

(30) Foreign Application Priority Data
Feb. 20, 2015 (IN) .......................... 567/MUM/2015

(51) Int. Cl.
G08B 13/16 (2006.01)
(52) U.S. Cl.
CPC ..... *G08B 13/1672* (2013.01); *G08B 13/1681* (2013.01); *G01N 2291/045* (2013.01); *G01N 2291/26* (2013.01)

(58) Field of Classification Search
CPC ....... G01N 2291/045; G01N 2291/048; G01N 2291/051; G01N 2291/052;
(Continued)

(56) References Cited

U.S. PATENT DOCUMENTS 5,035,144 A * 7/1991 Aussel ................. G01N 29/075
73/602
5,257,544 A * 11/1993 Khuri-Yakub ......... G01H 13/00
73/579

(Continued)

OTHER PUBLICATIONS

International Search Report dated Jul. 26, 2016, in counterpart International Application No. PCT/IB2016/050810; 2 pages.

(Continued)

*Primary Examiner* — Van Trieu
(74) *Attorney, Agent, or Firm* — Finnegan, Henderson, Farabow, Garrett & Dunner LLP

(57) ABSTRACT

An acoustic array system for anomaly detection is provided. The acoustic array system (100) performs a scan (or a progressive scan of frequencies) of a given volume by transmitting one or more signals, and receives one or more reflected signals from objects within the volume. The reflected signals are then amplified and converted to a set of digital signals. Features of the set of digital signals are extracted both in time and frequency domains. The acoustic array system (100) further performs a comparison of these set of digital extracted features with the reflected signals via machine learning techniques. Based on the comparison, the acoustic array system detects one or more anomalies.

20 Claims, 9 Drawing Sheets

(58) Field of Classification Search
CPC ....... G01N 2291/055; G01N 2291/056; G01N 2291/057; G01N 2291/10; G01N 2291/26; G01N 2291/262; G01N 2291/263; G01N 2291/265; G01N 2291/269; G01N 2291/04; G01N 2291/0422; G01N 2291/0423; G01N 2291/0425; G01N 2291/0426; G01N 2291/0427; G01N 2291/0428; G01S 15/523; G08B 13/1672; G08B 13/1681; G08B 29/186

See application file for complete search history.

(56) References Cited

U.S. PATENT DOCUMENTS

| | | | |
|---|---|---|---|
| 5,955,669 A * | 9/1999 | Egami | G01N 29/11 |
| | | | 73/579 |
| 9,396,632 B2 * | 7/2016 | Brav | G08B 13/1672 |
| 9,767,661 B2 * | 9/2017 | Brav | G08B 13/1672 |
| 2004/0003662 A1 * | 1/2004 | Kenderian | G01N 29/12 |
| | | | 73/579 |
| 2005/0092059 A1 | 5/2005 | Gessert et al. | |
| 2005/0146433 A1 | 7/2005 | Waltermann | |
| 2009/0301198 A1 * | 12/2009 | Sohn | G01N 29/069 |
| | | | 73/598 |
| 2011/0009746 A1 | 1/2011 | Tran et al. | |
| 2013/0006623 A1 | 1/2013 | Chelba et al. | |
| 2015/0020614 A1 | 1/2015 | Gettings et al. | |

OTHER PUBLICATIONS

Written Opinion dated Jul. 26, 2016, in counterpart International Application No. PCT/IB2016/050810; 7 pages.

* cited by examiner

ANOMALY DETECTION SYSTEM AND METHOD

PRIORITY CLAIM

This application is a U.S. National Stage Filing under 35 U.S.C. § 371 and claims priority from International Application No. PCT/IB2016/050810, filed on Feb. 16, 2016, which application claims priority under 35 U.S.C. § 119 from India Application No. 567/MUM/2015, filed on Feb. 20, 2015. The entire contents of the aforementioned application are incorporated herein by reference.

TECHNICAL FIELD

The embodiments herein generally relate to signal analysis, and, more particularly, to anomaly detection system and method.

BACKGROUND

Surveillance is a process of monitoring of objects such as humans, non-humans, and other objects, for the purpose of identifying unusual pattern in movements, activities, or other changing information leading to detection of anomalies. This is typically achieved by employing cameras in the location of interest in real environments such as a room. There are applications for detecting anomalies by identifying unusual patterns of movements for suspicious activity in the room. These applications involve the use of imaging techniques such as deploying low-resolution sensors. However, low-resolution sensors are unable to provide sufficient information by themselves with detailed inferences for unusual environmental conditions (e.g., darky, smoky or foggy conditions). Alternatively, high-resolution sensors (e.g., cameras) are deployed to cover large area. These cameras are not only expensive, but also are obtrusive, require multiple installations, adding additional cost to the infrastructures, thus leading to privacy issues. It is also important to ensure that the details which are captured is accurate without a trade-off in cost, privacy and environmental conditions.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below. In view of the foregoing, an embodiment herein provides anomaly detection systems and methods.

In one aspect, an anomaly detection method is provided. The method comprising: (i) insonifying at a first time interval, by using an acoustic array system, a volume at one or more predetermined frequencies from a first location by transmitting one or more signals; (ii) receiving one or more reflected signals from one or more objects in the first location based on the one or more transmitted signals; (iii) repeating the steps (i) till (ii) until a last location in the volume is insonified to obtain a first set of reflected signals; (iv) amplifying the first set of reflected signals to obtain a set of amplified signals; (v) converting the set of amplified signals to a set of digital signals; (vi) performing a comparison of the set of digital signals with the first set of reflected signals; and (vii) detecting, at the first time interval, one or more anomalies based on the comparison.

In an embodiment, the method may further comprise extracting one or more features from the set of digital signals in at least one of a time domain and a frequency domain, wherein the one or more extracted features comprises at least one of an amplitude or a duration per each insonified frequency, power spectral density and frequency. The step of performing a comparison comprises analyzing for one or more variations in the one or more extracted features of the set of digital signals with respect to one or more features with reference to at least one of the first set of reflected signals, and wherein the one or more anomalies are detected based on the one or more variations.

The method further comprises generating an acoustic map specific to the volume based on the one or more extracted features and the first set of reflected signals with respect to the first set of reflected signals; training the acoustic array system based on the acoustic map generated, wherein when the acoustic array system is trained, the acoustic array system comprises training data.

The method further comprises determining, using the trained acoustic array system, number of frequency scans required for insonifying the volume with specific direction at a second time interval based on at least one of the training data, the one or more variations, addition of one or more objects, removal of the one or more objects, a change in location of the one or more objects/persons in the volume, and the first set of reflected signals; and detecting, using the trained acoustic array system, one or more anomalies at the second time interval in the volume. In an embodiment, the first set of reflected signals are a set of baseline signals that are used as a reference and compared with a second set of reflected signals obtained from one or more objects at the second time interval to detect the one or more anomalies during the second time interval. In an embodiment, range of the one or more predetermined frequencies is greater than or equal to 20 kilo Hertz (kHz) i.e., above the human audible range.

In another aspect, an acoustic array system is provided. The acoustic array system comprises one or more transmitters that are configured to transmit, at a first time interval, one or more signals at one or more predetermined frequencies, for insonifying a volume from a first location; one or more receivers that are configured to receive one or more reflected signals from one or more objects in the first location based on the one or more transmitted signals, wherein the one or more signals are transmitted until a last location in the volume is insonified to obtain a first set of reflected signals; a microphone pre-amplification unit that is configured to amplify the first set of reflected signals to obtain a set of amplified signals; a multi-channel synchronous analog to digital converter (ADC) that is configured to convert the set of amplified signals to a set of digital signals; and a processor that is configured to perform a comparison of the set of digital signals with the first set of reflected signals, and detect, at the first time interval, one or more anomalies based on the comparison.

In an embodiment, one or more features are extracted from the set of digital signals by the processor in at least one of a time domain and a frequency domain. The one or more extracted features comprises at least one of an amplitude or a duration per each insonified frequency, power spectral density and frequency. In an embodiment, the processor is configured to perform a comparison by analyzing for one or more variations in the one or more features of the set of digital signals with respect to one or more features of the first set of reflected signals. In an embodiment, the one or more anomalies may be detected based on the one or more variations. In another embodiment, the one or more anomalies are detected based on at least one of a position and a distance of the one or more receivers from the one or more objects.

The processor is further configured to generate an acoustic map specific to the volume based on the one or more extracted features and the first set of reflected signals with respect to the first set of reflected signals. The processor is further configured to execute, one or more machine learning techniques stored in a memory, to train the acoustic array system in at least one of the time domain and the frequency domain based on the acoustic map generated, and wherein when the acoustic array system is trained, the acoustic array system comprises training data.

The trained acoustic array system is configured to determine number of frequency scans required for insonifying the volume with specific direction at a second time interval based on at least one of the training data, the one or more variations, addition of one or more objects, removal of the one or more objects, a change in location of the one or more objects in the volume, and the first set of reflected signals, and detect one or more anomalies at the second time interval in the volume. In an embodiment, the first set of reflected signals are a set of baseline signals that are used as a reference and compared with a second set of reflected signals obtained from one or more objects at the second time interval to detect the one or more anomalies. In an embodiment, range of the one or more predetermined frequencies is greater than or equal to 20 kilo Hertz (kHz).

In yet another aspect, one or more non-transitory machine readable information storage mediums comprising one or more instructions is provided. The instructions when executed by one or more acoustic array systems, (i) insonify at a first time interval, by using an acoustic array system, a volume at one or more predetermined frequencies from a first location by transmitting one or more signals; (ii) receive one or more reflected signals from one or more objects in the first location based on the one or more transmitted signals; (iii) repeat the steps (i) till (ii) until a last location in the volume is insonified to obtain a first set of reflected signals; (iv) amplify the first set of reflected signals to obtain a set of amplified signals; (v) convert the set of amplified signals to a set of digital signals; (vi) perform a comparison of the set of digital signals with the first set of reflected signals; and (vii) detect, at the first time interval, one or more anomalies based on the comparison.

In an embodiment, the instructions may further comprise extracting one or more features from the set of digital signals in at least one of a time domain and a frequency domain, wherein the one or more extracted features comprises at least one of an amplitude or a duration per each insonified frequency, power spectral density and frequency. The step of performing a comparison comprises analyzing for one or more variations in the one or more extracted features of the set of digital signals with respect to one or more features of the first set of reflected signals, and wherein the one or more anomalies are detected based on the one or more variations.

The instructions further comprises generating an acoustic map specific to the volume based on the one or more extracted features and the set of reflected signals with respect to the one or more transmitted signals; training the acoustic array system based on the acoustic map generated, wherein when the acoustic array system is trained, the acoustic array system comprises training data.

The instructions further comprises determining, using the trained acoustic array system, number of frequency scans required for insonifying the volume with specific direction at a second time interval based on at least one of the training data, the one or more variations, addition of one or more objects, removal of the one or more objects, a change in location of the one or more objects in the volume, and the first set of reflected signals; and detecting, using the trained acoustic array system, one or more anomalies at the second time interval in the volume. In an embodiment, the set of reflected signals are a set of baseline signals that are used as a reference and compared with another set of reflected signals obtained from one or more objects at the second time interval to detect the one or more anomalies. In an embodiment, range of the one or more predetermined frequencies is greater than or equal to 20 kilo Hertz (kHz).

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

BRIEF DESCRIPTION OF THE DRAWINGS

The embodiments herein will be better understood from the following detailed description with reference to the drawings, in which.

DETAILED DESCRIPTION

Figure 1:
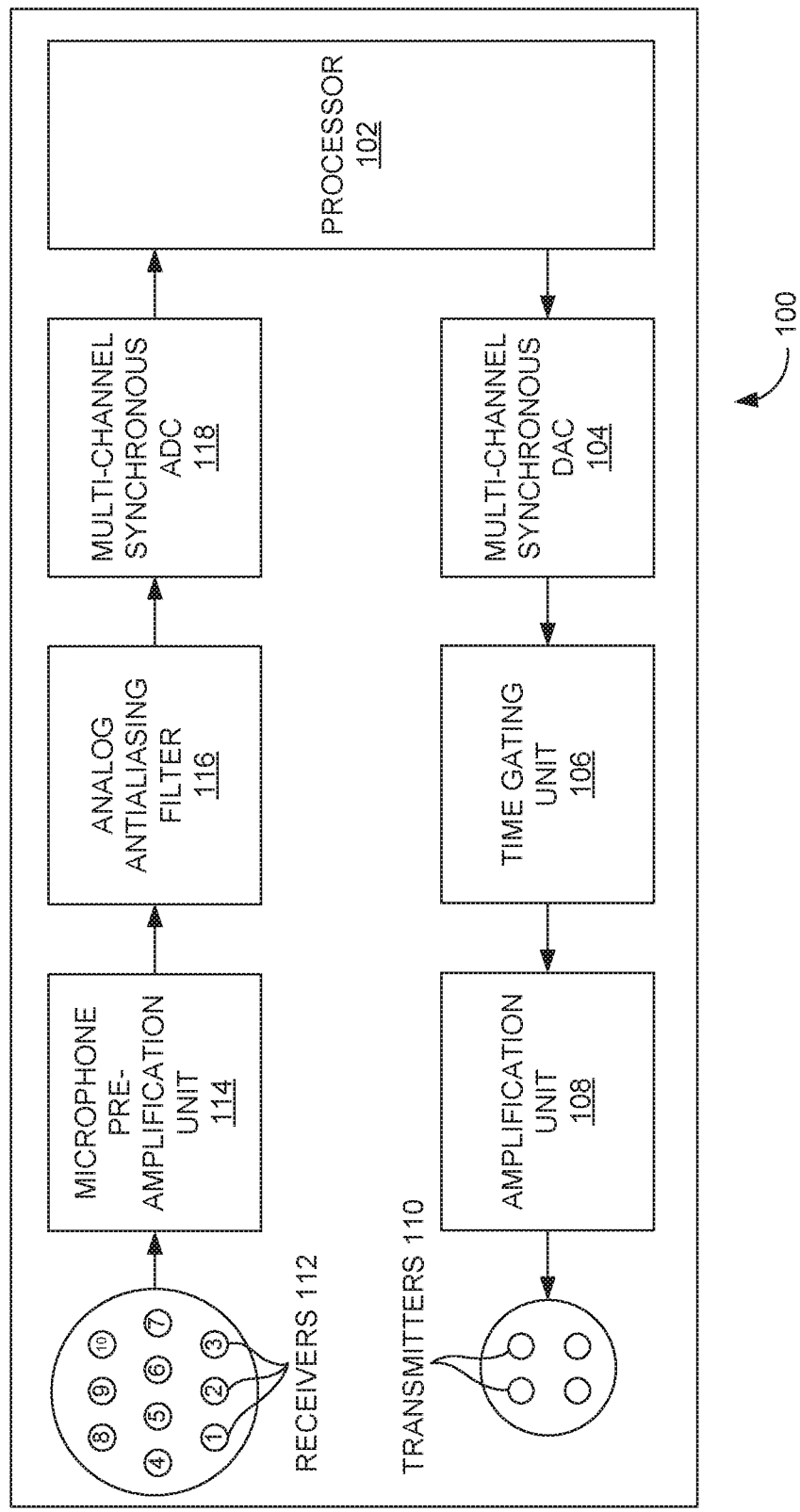
FIG. 1 illustrates a block diagram of an acoustic array system according to an embodiment of the present disclosure.

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

Some embodiments of this disclosure, illustrating all its features, will now be discussed in detail. The disclosed embodiments are merely exemplary of the disclosure, which may be embodied in various forms.

Before setting forth the detailed explanation, it is noted that all of the discussion below, regardless of the particular implementation being described, is exemplary in nature, rather than limiting.

The embodiments herein provide an acoustic array system and method for anomalies detection. The acoustic array performs a scan (or a progressive scan of frequencies) of an indoor environment (a given location such as a room) by transmitting one or more signals. One or more reflected signals are received from the objects within the room. One or more features are extracted from the reflected signals in time and frequency domain or a fusion of both, using one or more machine learning techniques by employing adaptive weighting techniques to detect the anomaly occurrence. The acoustic array is trained in both an online mode and as well as in an offline mode by using an artificial neural network/other machine learning techniques. This enables the acoustic array to learn from the training data, and identifying anomalies detection pattern. The acoustic array system is self-trained with reference data in the time and frequency domains (e.g., reference data such as available training data in at least one of the time domain and the frequency domain).

Referring now to the drawings, and more particularly to FIGS. 1 through 7D, where similar reference characters denote corresponding features consistently throughout the figures, there are shown preferred embodiments and these embodiments are described in the context of the following exemplary system and/or method.

FIG. 1 illustrates a block diagram of an acoustic array system 100 according to an embodiment of the present disclosure. The acoustic array system 100 comprises a processor 102, a multi-channel synchronous digital to analog converter (DAC) 104, a time gating unit 106, an amplification unit 108, one or more transmitters 110, one or more receivers 112, a microphone pre-amplification unit 114, an analog antialiasing filter 116, and a multi-channel synchronous analog to digital converter (ADC) 118. The processor 102 processes one or more acoustic signals to be transmitted. The multi-channel synchronous DAC 104 receives the one or more acoustic signals and converts the one or more acoustic input signals to one or more analog signals. The time gating unit 106 triggers a switch to transmit one or more output signals (e.g., the one or more analog signals) after recording the one or more acoustic signals. The one or more acoustic signals, one or more acoustic input signals, and the one or more output signals may be interchangeably used herein. The amplification unit 108 amplifies the one or more analog signals to obtain one or more amplified signals and are transmitted to the one or more transmitters 110. The amplification unit 108 is a power amplifier, in one example embodiment. The one or more transmitters 110 transmit the one or more amplified signals for insonifying a given location (e.g., a room). Further, the one or more transmitters 110 transmit the one or more amplified signals (also referred to as "one or more transmitted signals") at a predetermined range of frequencies (e.g., ≥20 kilo Hertz (kHz)).

The one or more receivers 112 receive one or more reflected signals (e.g., reflected signal acoustic time series) from one or more objects in the given location (e.g., the room). The objects comprise of, but are not limited to humans, non-humans, etc., in one example embodiment. The one or more receivers 112 comprises of a microphone receiver array, in one example embodiment. The microphone pre-amplification unit 114 receives the one or more reflected signals from the one or more receivers 112 and amplifies the one or more reflected signals to obtain one or more amplified signals. The microphone pre-amplification unit 114 is a low noise device and boosts the signal strength thereby improving the signal-to-noise ratio (SNR). The microphone pre-amplification unit 114 is a signal pre-amplifier, in one example embodiment. The analog antialiasing filter 116 restricts the bandwidth of the one or more amplified signals to approximately to a sampling rate over a band of interest.

The multi-channel synchronous analog to digital converter (ADC) 118 converts the one or more amplified signals to one or more digital signals. The processor 102 performs a comparison of the one or more digital signals (e.g., the one or more reflected signals) and the one or more reflected signals. Further, the processor 102 measures a response with respect to the one or more transmitted signals based on the comparison. The processor 102 analyzes the response for variations from the one or more transmitted signals to determine an existence of an anomaly such as but not limited to an addition, or removal of objects or intruders. The variation may also include changes in room artefacts, in one example embodiment. The acoustic array system 100 employs a phased array beamforming technique(s) on the one or more reflected signals to extract one or more features.

The one or more features are extracted from the one or more reflected signals (e.g., the one or more digital signals or backscattered signals) of the given room by fusing information from time and frequency domains and an alert is notified when an anomaly is detected by insonifying the room over a broadband scan of frequencies. Fusing can be done at features level as well as at score level. The one or more features that are extracted in time domain comprise but are not limited to, an amplitude (or energy profiles) or a duration per each insonified frequency, in conjunction with features extracted in frequency domain such as power spectral density and frequency content, enable to find the anomaly for more accurate detection, including estimation of the time of occurrence of an anomaly. In other words, energy profiles are extracted from time domain and frequency domain features are augmented to detect the anomaly better than using only spectral information. This enables to estimate the time of occurrence of an anomaly. The acoustic array system 100 is mounted on a mobile platform and further implements electronic beam forming as well as Pan and Tilt to scan various directions to improve coverage area.

The processor 102 implements (or executes) one or more machine learning techniques by employing adaptive weighting techniques for feature extraction from the one or more reflected signals in the time and frequency domain and to detect the anomaly occurrence. This is achieved by training the acoustic array (also referred as 'system') by using an artificial neural network/other machine learning techniques. The acoustic array system 100 is trained in time and frequency domain, and in both an online mode and as well as in an offline mode. Unlike, conventional systems such as optical based systems, the acoustic array system 100 uses an indirect imaging mechanism which can be triggered to detect an occurrence of an anomaly based on the critical or high priority scenarios.

Figure 2:
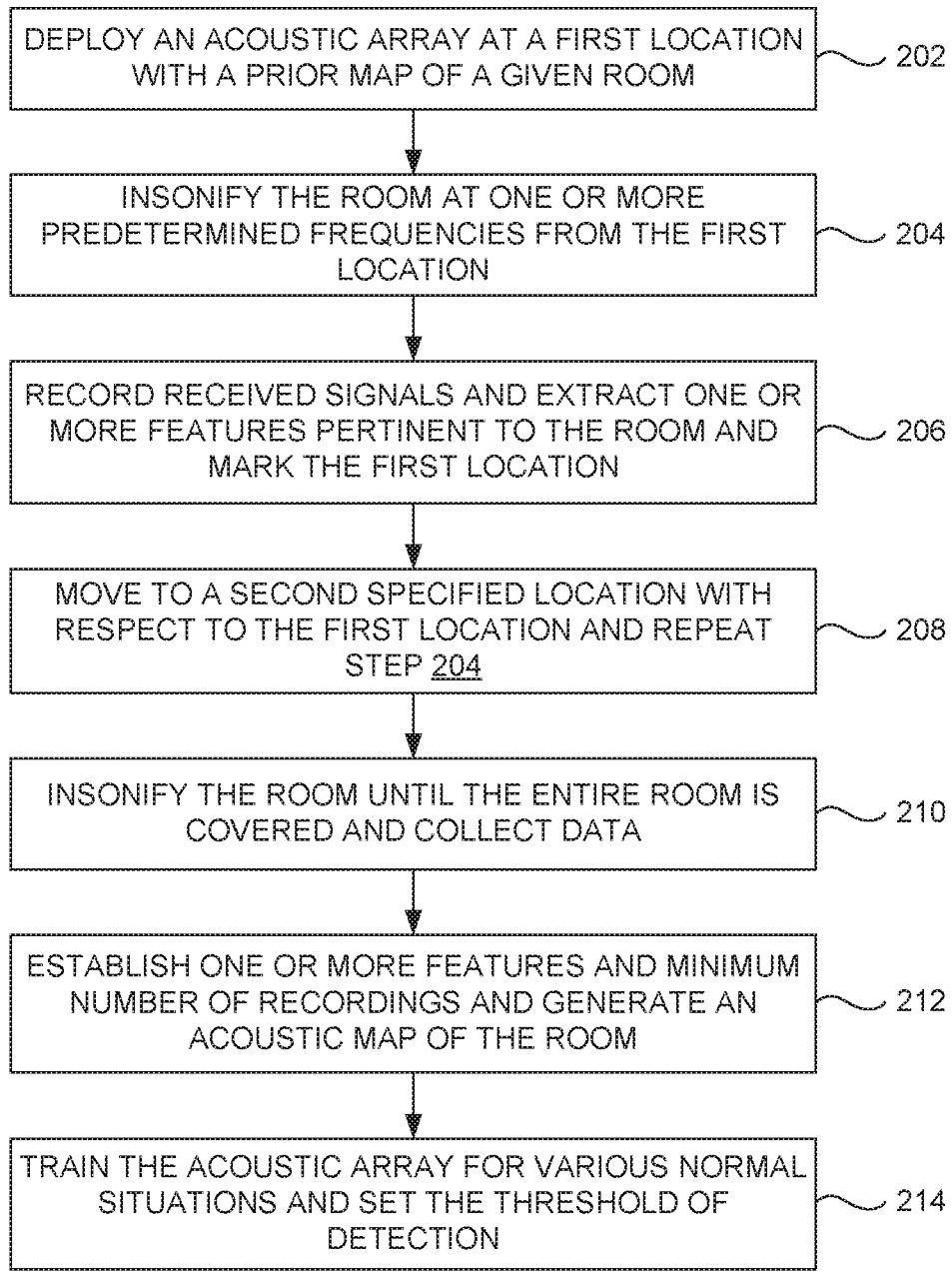
FIG. 2 is a flow diagram illustrating a method of detecting one or more anomalies using the acoustic array system of FIG. 1 according to an embodiment of the present disclosure.

With reference to FIG. 1, FIG. 2 is a flow diagram illustrating a method of detecting one or more anomalies using the acoustic array system 100 according to an embodiment of the present disclosure. In step 202, the acoustic array system 100 is deployed at a first location with a prior map of a given room. In step 204, the room is insonified at one or more predetermined frequencies from the first location and receive one or more reflected signals. The one or more transmitters 110 transmit one or more signals at the predetermined range of frequencies (or at least one predetermined frequency). In step 206, the received signals (e.g., the one or more reflected signals or one or more backscattered signals) are recorded and one or more features pertinent to the room are extracted from the one or more reflected signals or one or more backscattered signals and the first location is marked. In step 208, a second location is identified with respect to the first location and the room is insonified at the one or more predetermined frequencies from the second location (e.g., repeating the step 204).

In step 210, the step of insonifying the room is repeated until the entire room is covered and data is collected. It is to be understood that the step of insonifying the room is based on or depends on the room size, or other artefacts, etc., in one example embodiment. Therefore, the step 210, of insonifying the room from the second location may not be required when the room is small enough to be scanned in a single attempt. For example, when a room is small enough, the room is insonified by a single scan of frequency. In step 212, one or more features and minimum number of recordings are established, based on which an acoustic map of the room is generated. In step 214, the acoustic array system 100 is trained for various normal situations and the threshold for anomaly detection is set (or configured). Based on the training data available for a given room (or rooms), the acoustic array system 100 determines the number of frequency scans (e.g., progressive scans) required for a room. For example, for a given room (3 meters×4 meters or 12 Square Meters), the acoustic array system 100 may have completed scanning in 2 attempts at a first time duration T1, with a predetermined band of frequencies×kHz set.

The scanned information is stored in a memory (not shown in FIG. 1), which is utilized by the acoustic array system 100 at a later stage for anomaly detection at a second time duration T2 (where T2=T1+x), where x comprises real numbers. These features are extracted and recorded in a library and archived for training the system. In other words, the acoustic array system 100 performs the scanning in 2 attempts by setting the frequency band to x kHz. This also reduces the training time for training the acoustic array system 100, since the training data is already available in the memory (or database).

Figure 3:
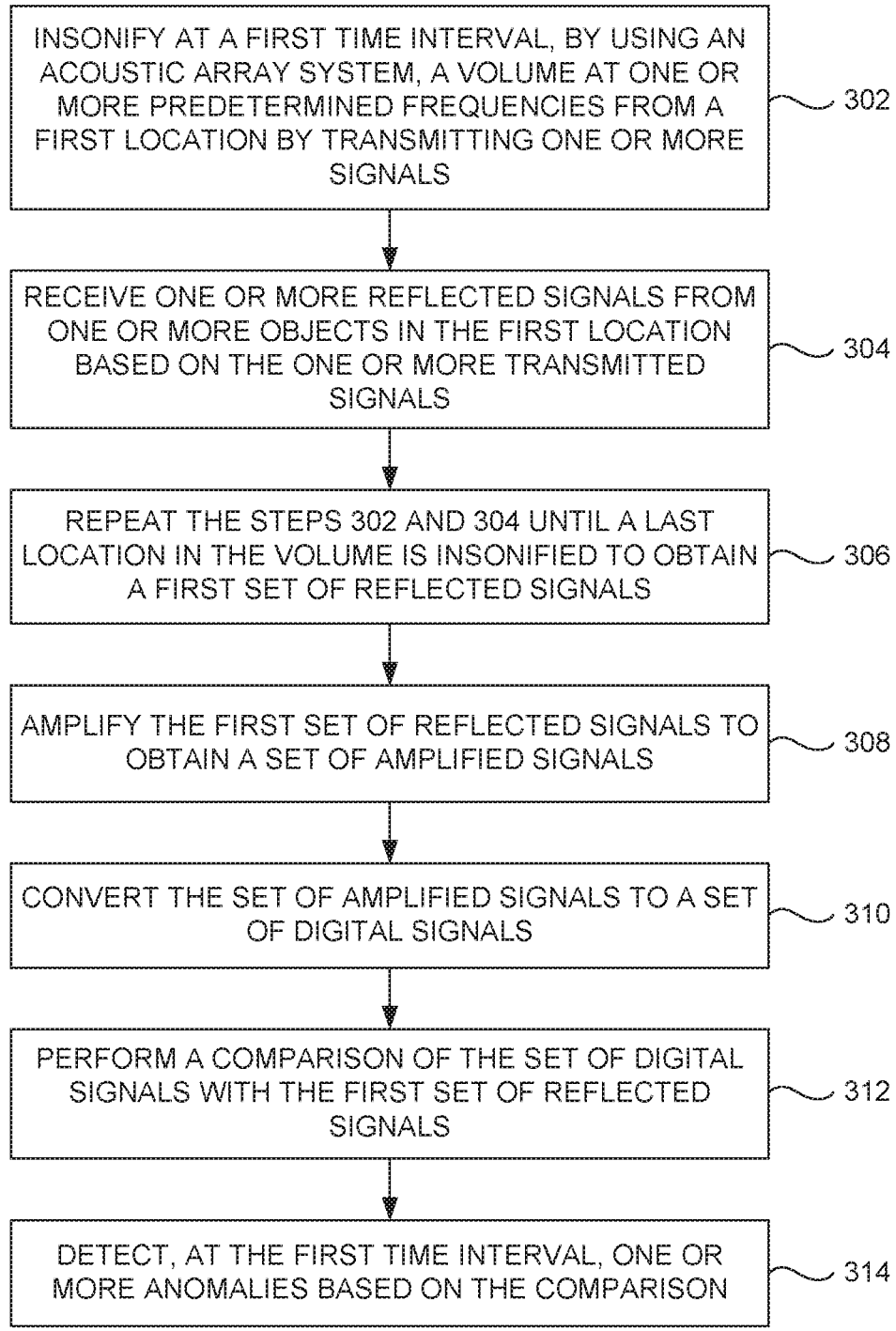
FIG. 3 is a flow diagram illustrating a method for anomaly detection using the acoustic array system of FIG. 1 according to an embodiment of the present disclosure.

FIG. 3, with reference to FIGS. 1 through 2, is a flow diagram illustrating a method for anomaly detection using the acoustic array system 100 of FIG. 1 according to an embodiment of the present disclosure. In step 302, a volume (or a given area) is insonified during a first time interval at one or more predetermined frequencies from a first location by transmitting one or more signals (e.g., using the one or more transmitters 110. In an embodiment, as described above, one or more acoustic signals are processed, converted to one or more analog signals, which are then amplified and transmitted for insonifying the volume. In one embodiment, the volume is a multi-dimensional volume, for example, a 2D or a 3D volume. In step 304, one or more reflected signals are received (e.g., by the one or more receivers 112) from one or more objects in the first location based on the one or more transmitted signals. In an embodiment, the number of reflected signals depend on number of objects in the volume. In step 306, the steps 302, and 304 are repeated until a last location in the volume is insonified to obtain a set of reflected signals (a first set). In an embodiment, the first location is the last location. In other words, when the volume is of smaller area, the entire volume may be insonified by the acoustic array system 100 from one location itself, and hence insonifying the volume from a second location may not be required.

In step 308, the first set of reflected signals are amplified (e.g., using the microphone pre-amplification unit 114 or also referred herein as an amplification unit) to obtain a set of amplified signals. In step 310, the set of amplified signals are converted to a set of digital signals (e.g., using multi-synchronous ADC 118 or also referred herein as ADC). In step 312, a comparison of the set of digital signals with the first set of signals is performed. In step, 314, one or more anomalies are detected during the first interval based on the comparison. In an embodiment, one or more features are extracted from the set of digital signals in at least one of a time domain and a frequency domain. The one or more extracted features comprises, but are not limited to, at least one of an amplitude or a duration per each insonified frequency, power spectral density and frequency.

The step of comparison comprises analyzing for one or more variations in the one or more extracted features of the set of digital signals with respect to one or more features of the first set of reflected signals. In an embodiment, the one or more variations in the one or more extracted features of the set of digital signals may be analyzed with respect to at least one of the one or more transmitted signals and the first set of reflected signals. In another embodiment, the one or more anomalies are detected based on the one or more variations. For example, a change (or variation) in frequency (or variation in frequency) from a reflected signal with respect to a frequency at which a corresponding signal was transmitted may enable the acoustic array system 100 to determine whether there is an anomaly detection or not. Further, an acoustic map specific to the volume may be generated based on at least one of the one or more extracted features and the first set of reflected signals with respect to the one or more transmitted signals.

The method may further comprise training the acoustic array system based on the acoustic map generated for the volume. The acoustic array system 100 may be trained using one or more machine learning techniques stored in the memory, or obtained from one or more sources, in one example embodiment. When the acoustic array system is trained, training data may be (or gets stored) in a memory (not shown in FIGS. 1-3). The method may further comprise determining, using the trained acoustic array system, number of frequency scans required for insonifying the volume with specific direction at a second time interval based on at least one of the training data, the acoustic map generated, the one or more variations, addition of one or more objects, removal of the one or more objects, a change in location of the one or more objects in the volume, and the first set of reflected signals, and detecting one or more anomalies at the second time interval in the volume. In an embodiment, the first set of reflected signals act as a set of baseline signals that are used as a reference and compared with a second set of reflected signals obtained from one or more objects at the second time interval to detect one or more anomalies in the volume during the second time interval. In other words, the first set of reflected signals are configured (or set) as a set of baseline signals by the processor 102 or the acoustic array system 100, such that the first set of reflected signals (or set of baseline signals) are used (by the processor 102 or the acoustic array system 100) as a reference and compared with a second set of reflected signals obtained from one or more objects at the second time interval to detect one or more anomalies in the volume during the second time interval. For instance, one or more features are extracted from the first set of reflected signals to obtain a first set of extracted features. Similarly, one or more features are extracted from the second set of reflected signals to obtain a second set of extracted features. The first set of features are the compared with the second set of extracted features and are analyzed for one or more variations in the second set of features.

Based on one or more variations in the second set of extracted features extracted from the second set of reflected signals received from one or more objects at the second time interval in comparison to the first set of extracted features, one or more anomalies are detected during the second time interval. The first time interval and the second time interval are different from each other. For instance, the first time interval may be Dec. 25, 2015, and the second time interval may be Dec. 31, 2015. In an embodiment, the one or more anomalies are detected based on at least one of a position (e.g., orientation) and a distance (near to, or far from) of the one or more receivers 112 (or the one or more transmitters 110) from one or more objects in a volume (or an area, for example, a room).

Figure 4:
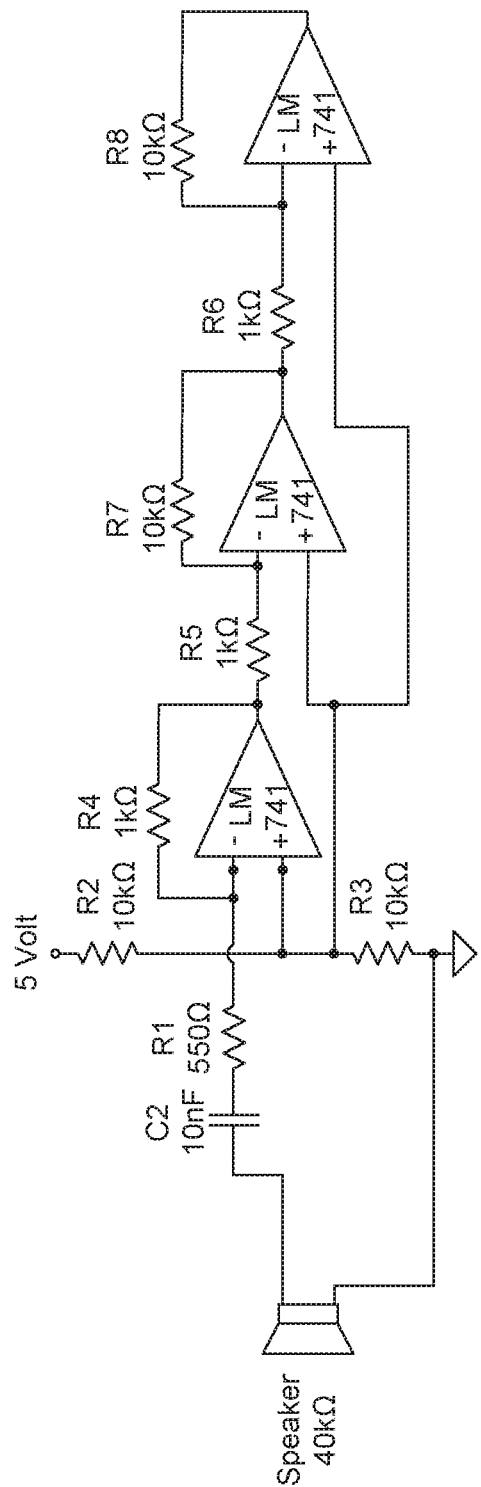
FIG. 4 is an exemplary representative circuit diagram of acoustic sensor array used in the acoustic array system of FIG. 1 according to an embodiment of the present disclosure.

FIG. 4, with reference to FIGS. 1 through 3, is an exemplary representative circuit diagram of acoustic sensor array used in the acoustic array system 100 of FIG. 1 according to an embodiment of the present disclosure. The acoustic sensor array consists of one or more ultrasonic transmitter modules (e.g., HC-SR04) and one or more ultrasonic receivers (e.g., 16 (4×4) of 'x' kHz frequency (e.g., 40 kHz) mounted on a mobile robot (e.g., or an object). In an embodiment, the spacing between the one or more transmitters 110 and the one or more receivers 112 needs to be properly designed. During the experimental tests, as the operating frequency is 40 kHz and speed of sound in air was approximately 340 m/sec, the distance between two consecutive receivers was 1 cm. Each receiver consisted of a 30 kHz High Pass Filter (HPF) and two-stage OPAMP amplifier as shown in FIG. 4. The overall gain of the amplifier is 200 approximately. It is to be understood to a person having ordinary skill in the art that number of components, for example, resistors, and Operational Amplifiers may vary based on the designs, requirements, volume(s), area(s), and the like to be insonified for anomaly detection. Similarly, the corresponding values of resistor(s) (e.g., 10 kilo Ohm (kΩ), 1 kilo Ohm (kΩ), 550 Ohm (Ω)), capacitor(s) (e.g., C2=10 Nano Farads (nF)) and including model of Operational Amplifiers (LM 741), and specifications of the components may vary (or change) based on the designs, requirements, volumes/areas to be insonified for anomaly detection.

Figure 5:
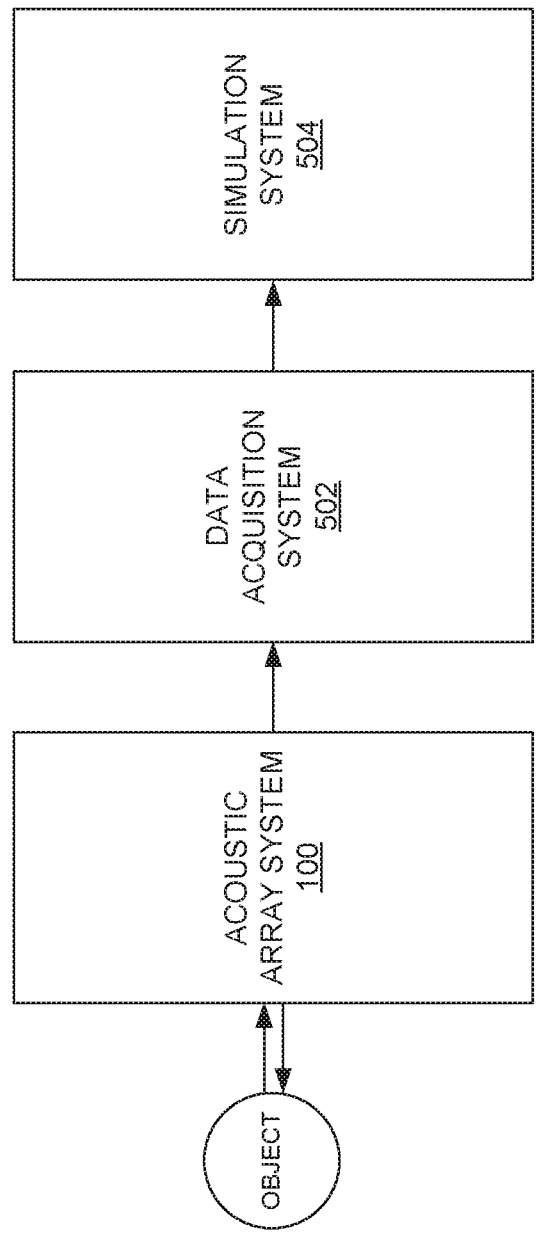
FIG. 5 is a block diagram illustrating the acoustic array system of FIG. 1 operatively connected to a data acquisition system that is operatively connected to a simulation system according to an embodiment of the present disclosure.

FIG. 5, with reference to FIGS. 1 through 4, is a block diagram illustrating the acoustic array system 100 operatively connected to a data acquisition system 502 that is operatively connected to a simulation system 504 according to an embodiment of the present disclosure. For analyzing the one or more reflected signals, the data acquisition system 502 (e.g., NI USB 6216) was connected to the acoustic array system 100, which has 'n' analog input channels (e.g., 16 analog input channels and one or more receivers (16 receivers)) to sample the signals at a sampling frequency of 400 kHz (10 times of the transmitted signals) per channel. One of the advantages of the data acquisition system 502 is that it can send the data to the simulation system 504 (or a simulation application), for example, a MATLAB simulation application for generating one or more graphical representations indicative of one or more anomalies being detected.

Figure 6A:
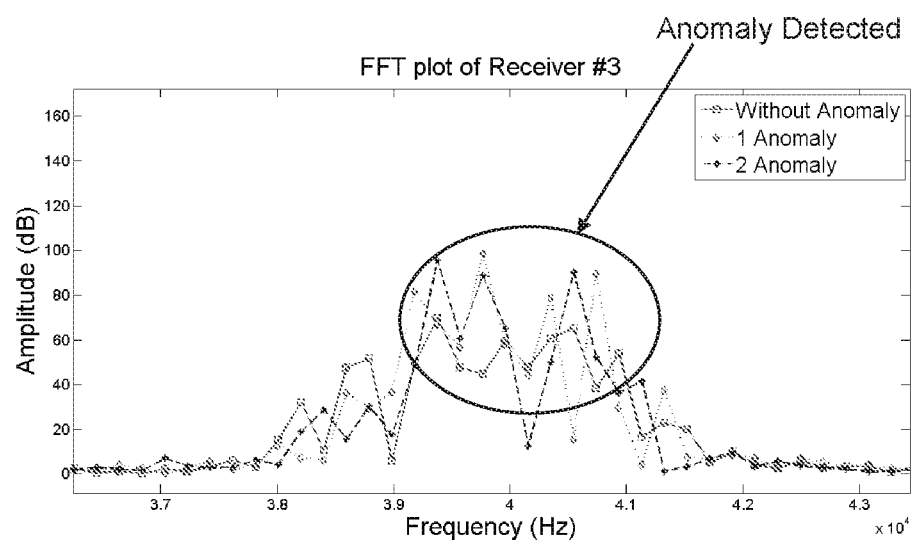
FIG. 6A depicts a Fast Fourier transform (FFT) plot for one or more reflected signals received by a third receiver of the acoustic array system of FIG. 1 according to an embodiment of the present disclosure.
Figure 6B:
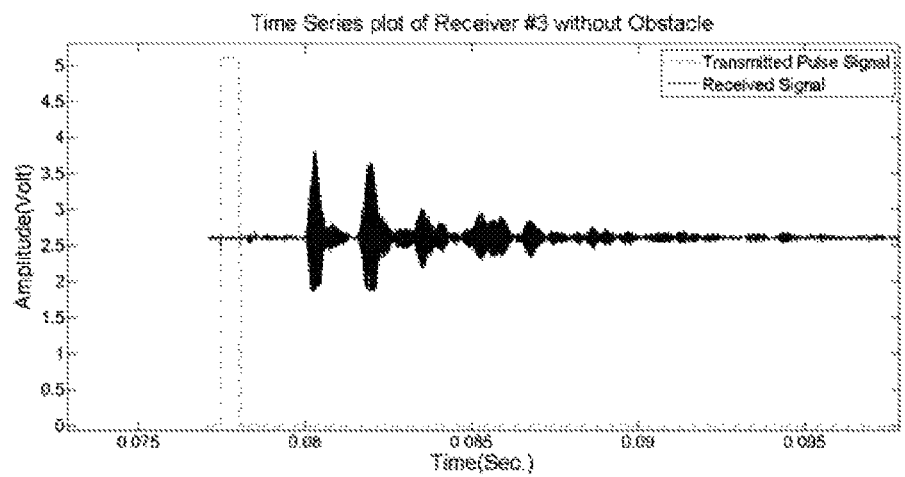
FIG. 6B depict time series plot of the third receiver without anomaly situation (or without obstacle) in time domain against amplitude (in volts) according to an embodiment of the present disclosure.
Figure 6C:
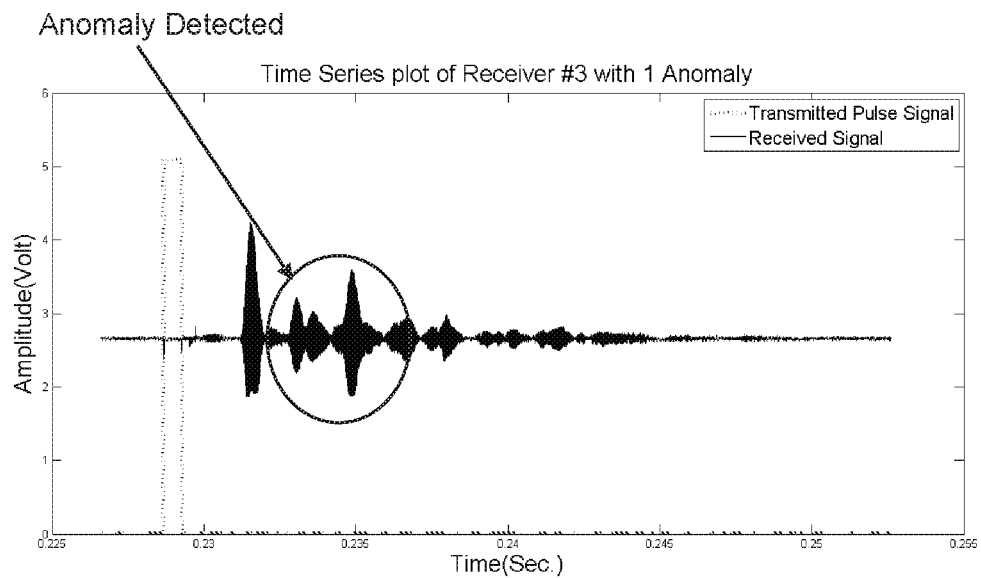
FIG. 6C depicts time series plot of the third receiver with one anomaly condition in time domain against amplitude (in volts) according to an embodiment of the present disclosure.
Figure 6D:
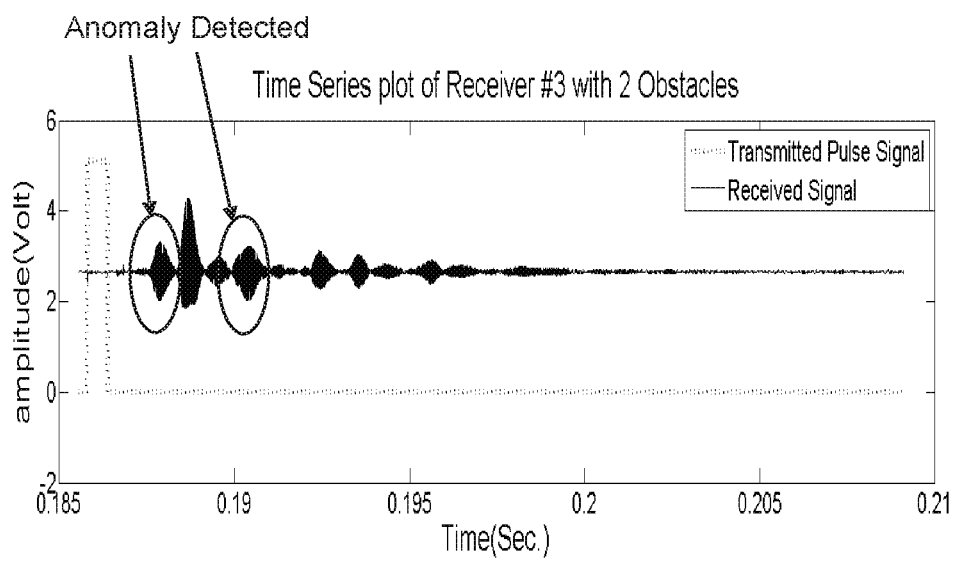
FIG. 6D depicts time series plot of the third receiver with two (2) anomaly condition in time domain against amplitude (in volts) according to an embodiment of the present disclosure.

FIG. 6A, with reference to FIGS. 1 through 5, is a graphical representation of with and without anomalies detection according to an embodiment of the present disclosure. More particularly, FIG. 6A, depicts a Fast Fourier transform (FFT) plot for one or more reflected signals received by a third receiver (e.g., denoted by 3 in FIG. 1) of the acoustic array system 100 of FIG. 1 according to an embodiment of the present disclosure. FIG. 6B depict time series plot of the third receiver without anomaly situation (or without obstacle) in time domain against amplitude (in volts) according to an embodiment of the present disclosure. FIG. 6C depicts time series plot of the third receiver with one anomaly condition in time domain against amplitude (in volts) according to an embodiment of the present disclosure. FIG. 6D depicts time series plot of the third receiver with two (2) anomaly condition in time domain against amplitude (in volts) according to an embodiment of the present disclosure. The time series plots clearly show that whenever anomaly(s) is/are present in the volume (e.g., a room), there is a change in corresponding received/reflected signal accordingly. This has been validated with the help of frequency plot against amplitude as shown in FIG. 6A.

Figure 7A:
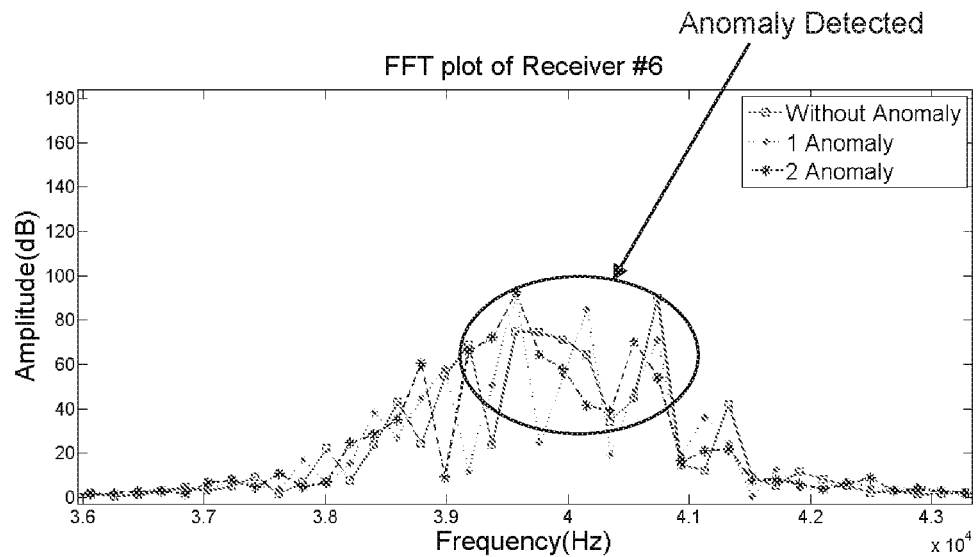
FIG. 7A depicts a Fast Fourier transform (FFT) plot for one or more reflected signals received by a sixth receiver of the acoustic array system of FIG. 1 according to an embodiment of the present disclosure.
Figure 7B:
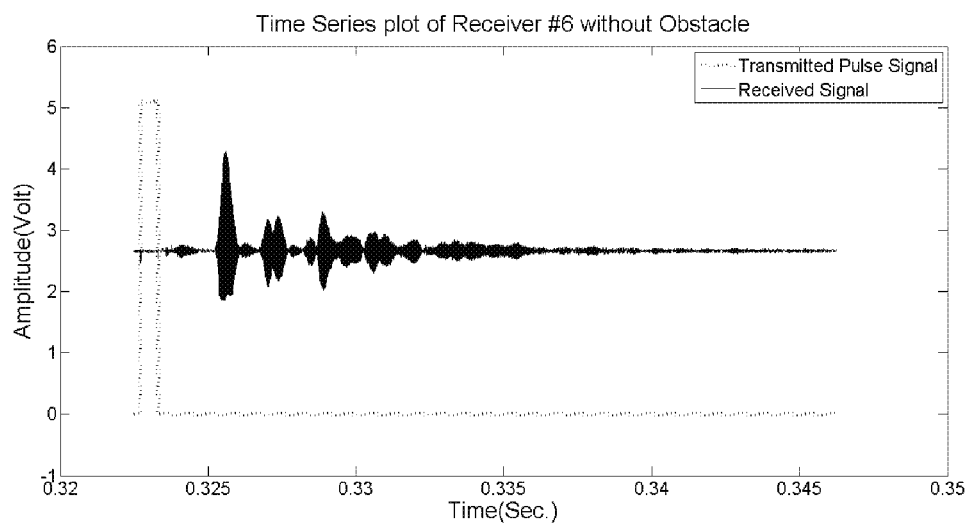
FIG. 7B depict time series plot of the sixth receiver without anomaly situation (or without obstacle) in time domain against amplitude (in volts) according to an embodiment of the present disclosure.
Figure 7C:
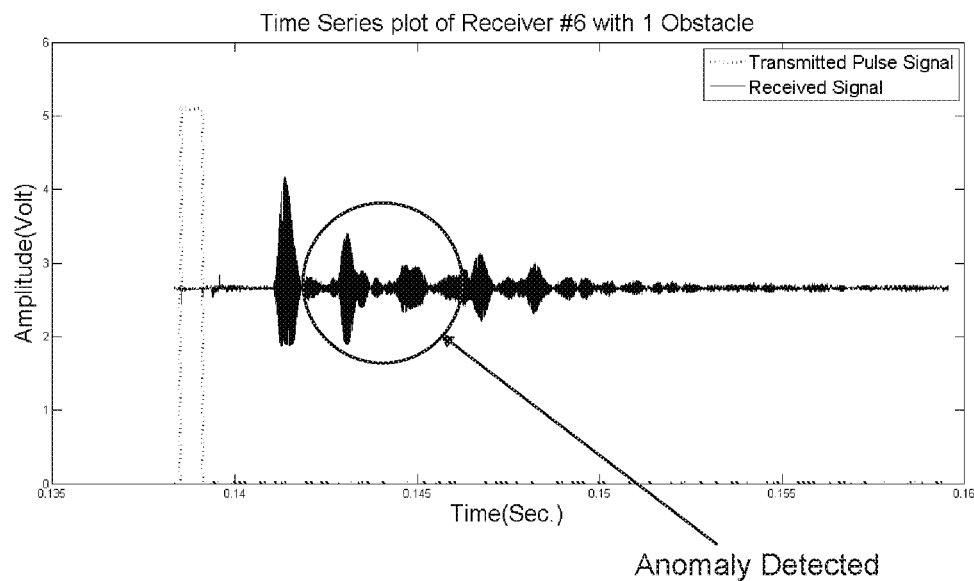
FIG. 7C depicts time series plot of the sixth receiver with one anomaly condition in time domain against amplitude (in volts) according to an embodiment of the present disclosure.
Figure 7D:
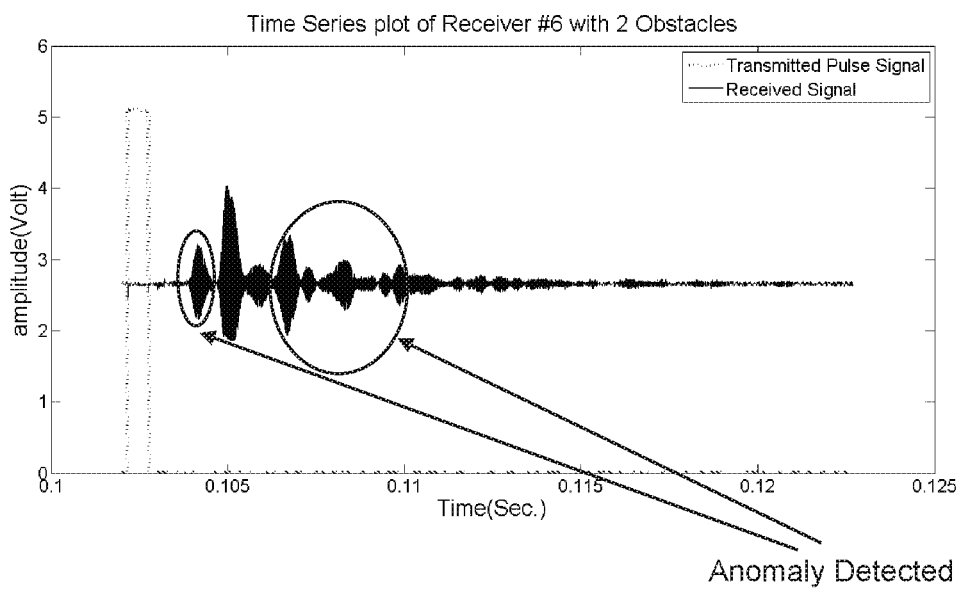
FIG. 7D depicts time series plot of the sixth receiver with two (2) anomaly condition in time domain against amplitude (in volts) according to an embodiment of the present disclosure.

FIG. 7A, with reference to FIGS. 1 through 6D, is a graphical representation of with and without anomalies detection according to an embodiment of the present disclosure. More particularly, FIG. 7A, depicts a Fast Fourier transform (FFT) plot for one or more reflected signals received by a sixth receiver (e.g., denoted by 6 in FIG. 1) of the acoustic array system 100 of FIG. 1 according to an embodiment of the present disclosure. FIG. 7B depict time series plot of the sixth receiver without anomaly situation (or without obstacle) in time domain against amplitude (in volts) according to an embodiment of the present disclosure. FIG. 7C depicts time series plot of the sixth receiver with one anomaly condition in time domain against amplitude (in volts) according to an embodiment of the present disclosure. FIG. 7D depicts time series plot of the sixth receiver with two (2) anomaly condition in time domain against amplitude (in volts) according to an embodiment of the present disclosure. The time series plots clearly show that whenever anomaly(s) is/are present in the volume (e.g., a room), there is a change in corresponding received/reflected signal accordingly. This has been validated with the help of frequency plot against amplitude as shown in FIG. 7A. The expression "transmitted pulse signal" is also referred as a transmitted signal. Similarly, the expression "received signal" is also referred as a reflected signal from one or more objects.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The acoustic array system 100 enables detecting variations in a room by removing/including objects within the room for surveillance and detection purposes/providing intruder alerts. The acoustic array system 100 may be mounted on any object for anomaly detection. The acoustic array system 100 comprises transmitters and receivers to insonify the room at a selected sweep of frequencies at selected locations and for measuring the response. This measured response is then analyzed for variations from the original signal to determine the existence of an anomaly i.e. addition/removal of objects/intruders. The embodiments described herein eliminates the need of installing repetitive sensory equipment, and also is capable of operating in stealth at ultrasonic frequencies and detecting anomalies even in dark and smoky environment where conventional optic based systems fail. The acoustic array system 100 operates in various ranges of environments and an optimal number of scans are decided based on the complexity and dimensions of the room. Since, the time domain data consists of information in terms of duration and amplitude/energy and spectral data contains energy spread over frequencies, the fusion offers a much larger data-set which is used for training and subsequently anomaly detection. Unlike optical based system which requires identification and detection of an anomaly, the acoustic array system 100 enables interaction between these acoustic backscattered/reflected data being pre-processed by adaptive weighting which comprise features that are the key to rapid and error proof anomaly detection.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments may include a hardware configuration of an information handling/computer system in accordance with the embodiments herein. The system herein comprises at least one processor or central processing unit (CPU). The CPUs are interconnected via system bus to various devices such as a random access memory (RAM), read-only memory (ROM), and an input/output (I/O) adapter. The I/O adapter can connect to peripheral devices, such as disk units and tape drives, or other program storage devices that are readable by the system. The system can read the inventive instructions on the program storage devices and follow these instructions to execute the methodology of the embodiments herein.

The system further includes a user interface adapter that connects a keyboard, mouse, speaker, microphone, and/or other user interface devices such as a touch screen device (not shown) to the bus to gather user input. Additionally, a communication adapter connects the bus to a data processing network, and a display adapter connects the bus to a display device which may be embodied as an output device such as a monitor, printer, or transmitter, for example.

The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

We claim:

1. A method comprising:
    (i) insonifying at a first time interval, by using an acoustic array system, a volume at one or more predetermined frequencies from a first location by transmitting one or more signals;
    (ii) receiving one or more reflected signals from one or more objects in said first location based on said one or more transmitted signals;
    (iii) repeating the steps (i) till (ii) until a last location in said volume is insonified to obtain a first set of reflected signals;
    (iv) amplifying said first set of reflected signals to obtain a set of amplified signals;
    (v) converting said set of amplified signals to a set of digital signals;
    (vi) performing a comparison of said set of digital signals with said first set of reflected signals; and
    (vii) detecting, at said first time interval, one or more anomalies based on said comparison.

2. The method of claim 1, further comprising extracting one or more features from said set of digital signals in at least one of a time domain and a frequency domain, wherein said one or more extracted features comprises at least one of an amplitude or a duration per each insonified frequency, power spectral density and frequency.

3. The method of claim 2, wherein performing a comparison comprises analyzing for one or more variations in said one or more extracted features of said set of digital signals with respect to one or more features of at least one of said one or more transmitted signals and said first set of reflected signals, and wherein said one or more anomalies are detected based on said one or more variations.

4. The method of claim 3, further comprising generating an acoustic map specific to said volume based on said one or more extracted features of the set of digital signals and with respect to said first set of reflected signals.

5. The method of claim 4, further comprising training said acoustic array system based on said acoustic map generated, wherein when said acoustic array system is trained, said acoustic array system comprises training data.

6. The method of claim 5, further comprising
    determining, using said trained acoustic array system, number of frequency scans required for insonifying said volume with specific direction at a second time interval based on at least one of said training data, said one or more variations, addition of one or more objects, removal of said one or more objects, a change in location of said one or more objects in said volume, and said first set of reflected signals; and
    detecting, using said trained acoustic array system, one or more anomalies at said second time interval in said volume, wherein said first set of reflected signals are a set of baseline signals that are used as a reference and compared with a second set of reflected signals obtained at said second time interval to detect said one or more anomalies in said volume during said second time interval.

7. The method of claim 1, wherein range of said one or more predetermined frequencies is greater than or equal to 20 kilo Hertz (kHz).

8. An acoustic array system, comprising:
    one or more transmitters that are configured to transmit, at a first time interval, one or more signals at one or more predetermined frequencies, for insonifying a volume from a first location;
    one or more receivers that are configured to receive one or more reflected signals from one or more objects in said first location based on said one or more transmitted signals, wherein said one or more signals are transmitted until a last location in said volume is insonified to obtain a first set of reflected signals;
    a microphone pre-amplification unit that is configured to amplify said first set of reflected signals to obtain a set of amplified signals;
    a multi-channel synchronous analog to digital converter (ADC) that is configured to convert said set of amplified signals to a set of digital signals; and
    a processor that is configured to perform a comparison of said set of digital signals with said first set of reflected signals, and detect, at said first time interval, one or more anomalies based on said comparison.

9. The acoustic array system of claim 8, wherein one or more features are extracted from said set of digital signals in at least one of a time domain and a frequency domain, wherein said one or more extracted features comprises at least one of an amplitude or a duration per each insonified frequency, power spectral density and frequency.

10. The acoustic array system of claim 9, wherein said processor is configured to perform a comparison by analyzing for one or more variations in said one or more features of said set of digital signals with respect to one or more features of at least one of said one or more transmitted signals and said set of reflected signals, and wherein said one or more anomalies are detected based on said one or more variations.

11. The acoustic array system of claim 9, wherein said processor is further configured to generate an acoustic map specific to said volume based on said one or more extracted features and said first set of reflected signals with respect to said one or more transmitted signals.

12. The acoustic array system of claim 11, wherein said processor is further configured to execute, one or more machine learning techniques stored in a memory, to train said acoustic array system in at least one of said time domain and said frequency domain based on said acoustic map generated, and wherein when said acoustic array system is trained, said acoustic array system comprises training data.

13. The acoustic array system of claim 12, wherein said trained acoustic array system is configured to determine number of frequency scans required for insonifying said volume with specific direction at a second time interval based on at least one of said training data, said one or more variations, addition of one or more objects, removal of said one or more objects, a change in location of said one or more objects in said volume, and said first set of reflected signals, and detect one or more anomalies at said second time interval in said volume, wherein said set of reflected signals are a set of baseline signals that are used as a reference and compared with another set of reflected signals obtained at said second time interval to detect said one or more anomalies.

14. The acoustic array system of claim 8, wherein range of said one or more predetermined frequencies is greater than or equal to 20 kilo Hertz (kHz).

15. The acoustic array system of claim 8, wherein said one or more anomalies are detected based on at least one of a position and a distance of said one or more receivers from said one or more objects.

16. One or more non-transitory machine readable information storage mediums comprising one or more instructions which when executed by one or more acoustic array systems causes:
   (i) insonifying at a first time interval, by using an acoustic array system, a volume at one or more predetermined frequencies from a first location by transmitting one or more signals;
   (ii) receiving one or more reflected signals from one or more objects in the first location based on the one or more transmitted signals;
   (iii) repeating the steps (i) till (ii) until a last location in the volume is insonified to obtain a first set of reflected signals;
   (iv) amplifying the first set of reflected signals to obtain a set of amplified signals;
   (v) converting the set of amplified signals to a set of digital signals;
   (vi) performing a comparison of the set of digital signals with the first set of reflected signals; and (vii) detecting, at the first time interval, one or more anomalies based on the comparison.

17. The one or more non-transitory machine readable information storage mediums of claim 16, wherein the instructions which when executed by the one or more acoustic array systems further causes extracting one or more features from the set of digital signals in at least one of a time domain and a frequency domain, wherein the one or more extracted features comprises at least one of an amplitude or a duration per each insonified frequency, power spectral density and frequency.

18. The one or more non-transitory machine readable information storage mediums of claim 17, wherein the step of performing a comparison comprises analyzing for one or more variations in the one or more extracted features of the set of digital signals with respect to one or more features of the first set of reflected signals, and wherein the one or more anomalies are detected based on the one or more variations.

19. The one or more non-transitory machine readable information storage mediums of claim 18, wherein the instructions which when executed by the one or more acoustic array systems further causes
   generating an acoustic map specific to the volume based on the one or more extracted features and the set of reflected signals with respect to the one or more transmitted signals; and
   training the one or more acoustic array systems based on the acoustic map generated, wherein when the acoustic array system is trained, the acoustic array system comprises training data.

20. The one or more non-transitory machine readable information storage mediums of claim 19, wherein the instructions which when executed by the one or more acoustic array systems further causes
   determining, using the one or more trained acoustic array systems, number of frequency scans required for insonifying the volume with specific direction at a second time interval based on at least one of the training data, the one or more variations, addition of one or more objects, removal of the one or more objects, a change in location of the one or more objects in the volume, and the first set of reflected signals; and
   detecting, using the trained acoustic array system, one or more anomalies at the second time interval in the volume, wherein the set of reflected signals are a set of baseline signals that are used as a reference and compared with another set of reflected signals obtained from one or more objects at the second time interval to detect the one or more anomalies, wherein range of the one or more predetermined frequencies is greater than or equal to 20 kilo Hertz (kHz).

\* \* \* \* \*